United States Patent [19]

Carroll

[11] Patent Number: 4,844,061
[45] Date of Patent: Jul. 4, 1989

[54] MEDICAL TUBE HOLDER

[75] Inventor: John F. Carroll, Saratoga Springs, N.Y.

[73] Assignee: Ergomed, Inc., San Antonio, Tex.

[21] Appl. No.: 114,055

[22] Filed: Oct. 29, 1987

[51] Int. Cl.[4] .......................................... A01M 16/00
[52] U.S. Cl. ........................ 128/201; 128/DIG. 26; 604/179; 604/180
[58] Field of Search ................. 128/207.17, 200.26, 128/DIG. 26; 604/174, 179, 180

[56] References Cited

U.S. PATENT DOCUMENTS

| | | | |
|---|---|---|---|
| 3,927,676 | 12/1975 | Schultz | 128/DIG. 26 |
| 4,074,397 | 2/1978 | Rosin | 128/DIG. 26 |
| 4,142,257 | 3/1979 | Garcia | 604/180 |
| 4,548,200 | 10/1985 | Wapner | 128/207.17 |
| 4,622,034 | 11/1986 | Shattuck | 128/DIG. 26 |

*Primary Examiner*—Max Hindenburg
*Assistant Examiner*—K. M. Reichle
*Attorney, Agent, or Firm*—Bacon & Thomas

[57] ABSTRACT

A method tube holder and method for holding a trachael tube or the like in an intubated position in a patient are disclosed. The holder includes an elongated strip of resilient fabric having a porous or foam material bonded thereto. The strip includes an aperture at one end thereof which is adapted to fit over the portion of the medical tube that extends outside of the patient's mouth or nose so that the free or opposite end of the strip may be passed around the patient's head. An adhesive band is formed around the tube on the portion that extends outside of the patient and the free end of the elongated strip is adapted to be wrapped around the adhesive band and tube. A fastener such as a Velcro strip is also provided for fixing the free end of the elongated strip to an intermediate portion thereof along side of the patients's head.

3 Claims, 2 Drawing Sheets

MEDICAL TUBE HOLDER

BACKGROUND OF THE INVENTION

This invention relates to an improved medical tube holder and more particularly to a disposable device for securing an endotrachael tube or the like in place in an intubated patient. The present invention also relates to an improved method for holding an endotrachael tube or the like in an intubated position in a patient.

Many surgical procedures, as well as emergency medical treatments often require endotrachael or nasotrachael intubation. For example, intubation is frequently required in situations involving blockage of a patient's mouth, throat or trachael. In such cases, intubation may be provided by inserting an endotrachael tube through the patients mouth and into the trachael to a point just below the vocal cords, but above the bronchial tubes. And then, the tube must be securely maintained in this position.

One approach for maintaining an endotrachael tube in place is to attach the exposed end of the tube to the patient's face with adhesive tape. Unfortunately, this approach can take an excessive amount of time and a relatively high degree of skill may be required. Furthermore, if the tape means into contact with perspiration, saliva, blood or other fluids it may not adhere to the patient or may loosen and allow the tube to become displaced.

Therefore, there have been a number of approaches to provide trachael tube holders. For example, the patent of Bruce T. Shattuck U.S. Pat. No. 4,622,034 discloses a tube holder comprising a foam strip with one or more apertures therein. One of the apertures is placed over or around a portion of the trachael tube extending from the mouth of the patient. In one embodiment a second aperture is placed over the tube after the foam strip is passed around the head of the patient. An alternative embodiment suggest wrapping the strip around the tube and holding it in place with a Velcro fastener.

The aforementioned devices have been found to overcome many of the shortcomings attributed to the use of tape. Nevertheless, there is a continuing need for an improved holder. For example, there is a need for a medical tube holder and method which will more securely maintain the tube in place, minimize the likelihood that the holder slips with respect to the tube, does not require the application of an adhesive to the patient's skin, and minimizes the likelihood of a hook like fastener (Velcro strip) breaking the skin of the patient. In addition, an improved holder should be relatively inexpensive, simple to use and as comfortable as reasonably possible for the patient.

It has now been found that an improved medical tube holder and method according to the present invention provide the aforementioned characteristics.

SUMMARY OF THE INVENTION

In essence, an improved method for holding a trachael tube or the like in an intubated position in a patient includes the step of providing a trachael tube or the like having proximal and distal ends. The distal end is adapted to be intubated into a patient's air passage with the proximal end extending outside of the patient's mouth or nose. A band or ring of adhesive is formed around the circumference of the tube in the area which extends outside of the patient's body. And, an elongated flexible strip of resilient material is provided for holding the trachael tube in place. This flexible strip defines an aperture or opening at one end thereof. And, after intubation of the patient, the aperture is placed over the portion of the trachael tube which extends outside of the patient and the flexible strip is passed around the back of the patient's head and forward to a position adjacent to the tube. And then, the free end of the strip is wrapped around the adhesive ring to secure the tube in place.

In a preferred approach, there will be an excess length of flexible strip material provided. The strip is then cut, so that, after being wrapped around the tracheal tube at least one and one half times the free end extends back along the side of the patient's head. This free end is then attached to an intermediate portion of the elongated strip on the side of the patient's head with a small flexible strip of material including hooklike elements such as a piece of Velcro material. The Velcro material engages the elongated strip and holds the free end in place.

A disposable medical tube holding device according to the present invention includes an elongated flexible strip of resilient fabric material which has a soft skin engaging porous material molded onto one side thereof. The strip has a width which is substantially greater than the combined thickness of the strip and the skin engaging material, and defines an aperture which is adapted to pass over one end of the tube. The strip is also adapted to pass around the patients head or neck with the skin engaging material in contact with the patient. An adhesive band or ring is placed around the tube in the area which extends outside of the patients body. For example, a piece of double sided adhesive tape having one side covered with a nonadhesive peelable film is wrapped around the trachael tube and the peelable film removed to form a band or ring of adhesive. The free end of the elongated strip is constructed and arranged or adapted to be wrapped around the adhesive band with a portion thereof extending beyond the tube. And in a preferred embodiment of the invention, the band of adhesive has a width which is about the same as the width of the elongated strip, so that, the strip may be wrapped around the band of adhesive one or two times in order to provide a more secure hold on the tube. The strip is preferably wrapped around the tube one and one half times, however, a single wrap may be sufficient to fix the tube in place. But, the one and one half wraps around a single width of adhesive has been found preferable for obtaining the correct amount of tension on the trachael tube. The elongated strip is also preferable of sufficient length so that it extends beyond the tube after being wrapped around the tube to a position back along the side of a patient's head. And, a hooklike material strip such as a Velcro strip is then provided to fasten the elongated strip to an intermediate portion in a manner, so that, it will not come into contact with the face or skin of the patient.

The medical tube holder and method for holding a trachael tube or the like in an intubated position will now be described in detail in connection with the accompanying drawings.

DESCRIPTION OF THE PREFERRED EMBODIMENTS

Figure 1:
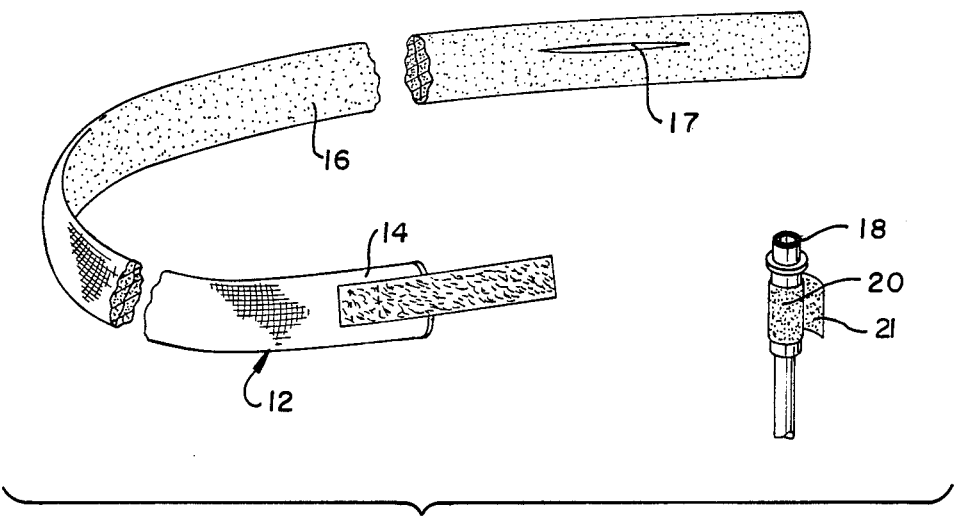
FIG. 1 is a side perspective view illustrating a medical tube holder according to one embodiment of the invention.
Figure 2:
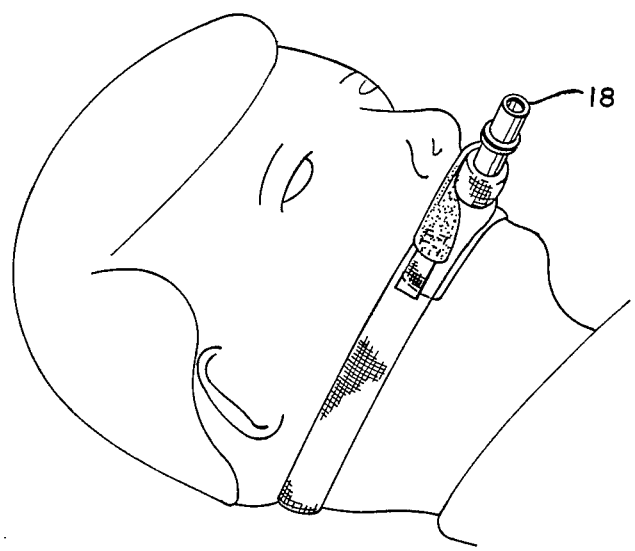
FIGS. 2 is a side perspective view illustrating the medical tube holder of FIG. 1 as it would be used to hold an endotrachael tube in an intubated position in a patient; and, FIG. 3 is a flow chart illustrating a method for holding a trachael tube or the like in an intubated position according to a preferred embodiment of the invention.

FIGS. 1 and 2 illustrate a medical tube holder according to one embodiment of the invention. The tube holder referred to generally as 10 is an elongated strip 12 of foam material, approximately three fourth's inch wide and about one third of an inch thick. A laminated combination of polyether foam and cotton vel mesh or other fabric material is preferred. These materials are, for example available from San Antonio Foam Fabrication of San Antonio, Tex., although other suitable materials with sufficient flexibility, resiliency, and cushioning qualities may be used. The strip 12 has a porous side 14 and a fabric side 16. The porous or foam side 14 is softer and therefore more comfortable against the skin of the patient because it may be made of a foam material. The fabric mesh is laminated or adhered as a backing onto the polyether foam which forms the porous side 14 of the device. The porous side 14 is turned toward the patient's skin, as shown in FIG. 2, because it is less irritating and more comfortable for the patient. The fabric side 16 is turned away from the patient's skin in order to provide a better grip on the overlapping portion of the holder and to prevent slippage of the tube as will be explained in more detail hereinafter. Also the fabric side 16 acts as a reinforcement backing for the polyether foam and prevents tearing of an aperture (to be described later) from tearing.

The strip 12 defines an aperture 17 in the center of the strip 12 at one end thereof. In general, the aperture or slit 17 is cut in the elongated strip 12 and is adapted to be placed over an endotrachael tube 18 or to have the tube 18 passed through the slit to thereby fix one end of the strip 12 of the holder 10 to the tube 18.

The holder 10 also includes an adhesive band or ring 20 which is adapted to be placed around the portion of the tube 18 that extends outside of the patient's mouth. In essence the adhesive ring 20 is made of a short piece of double sided adhesive tape such as a 3M product identified as Double Stick no. 34-713-7287-1 or similar product which is hypoallergenic. The tape is wrapped around the tube 18 to bond the holder 10 to the tube 18 in a manner that will prevent slippage of the holder 10 with respect to the tube 18. Each side of the double sided adhesive may be covered with a non-adhesive peelable film overlying the adhesive. One of the peelable films is then removed before applying the adhesive ring 20 around the tube 18, and, the second peelable film is removed so that the holder 10 can be wrapped around the adhesive ring 20.

As shown in FIG. 2, a patient is intubated with an endotrachael tube 18 and the aperture 17 i.e. that portion of an elongated strip 12 is pressed downwardly toward the lips of the patient. And then, a strip of double sided adhesive tape having a width of between about one-half inch and about one inch is wrapped around the tube 18 to form an adhesive ring 20. The width of the tape is preferably about three-fourths of an inch. The ring 20 is disposed above the portion of the holder that is adjacent the lips of the patient and relatively close to the end of tube 18. The adhesive strip has a length that is sufficient to completely encircle the tube 18.

In practice, the double sided tape is covered with a nonadhesive peelable film 21 on one side thereof which is removed from the tape after the ring 20 is formed.

The holder 10 is then wrapped around the patient's head with the porous side 14 adjacent to the patient's head. Care should be taken to avoid twisting of the elongated strip 12 since any twisting would add to the discomfort of the patient.

The holder 10 may be overlapped like a belt and may be cut to the approximate size according to the size of the patient's head. For example, in working with a relatively small child, a relatively short elongated strip would be preferred.

The elongated strip 12 is placed under slight tension to hold the tube 18 in a snug but comfortable position. And, because of the resiliency of the elongated strip 12 the free end thereof can be wrapped one and one half or two times around the tube 18 to provide the proper amount of tension on the tube 18 and hold it securely in place in an intubated position. Also, the porous side 14 of the elongated strip 12 will releasabley engage the patient's head and face to prevent movement of the holder 10 and tube 18. And, the cushioned properties provide greater comfort to the patient.

In practice, the free end of the elongated strip 12 is wrapped around the adhesive ring 20 and tube 18 one and one half times twice in a partially overlapping manner to more securely fix the tube 18 in place. The free end of the elongated strip 12 is then pulled back along itself or if the elongated strip is wrapped around the tube 18 twice it is pulled forwardly in the same direction into an overlapping position along the side of the patient's head. And then, a Velcro strip of other hooklike flexible material is pressed against the fabric side 16 of the free end and against an intermediate portion of the elongated strip 12 along side of the patients head. Placing the Velcro strip on the fabric side 16 of the elongated strip 12 in a location that is removed from the patient's face, minimizes the likelihood of the Velcro strip coming into contact with the patient's face or lips and eliminates the likelihood of breaking the patient's skin. For example, in using the prior art devices, patients have been found to have one or more of the hooklike elements embedded in one of their lips.

Figure 3:
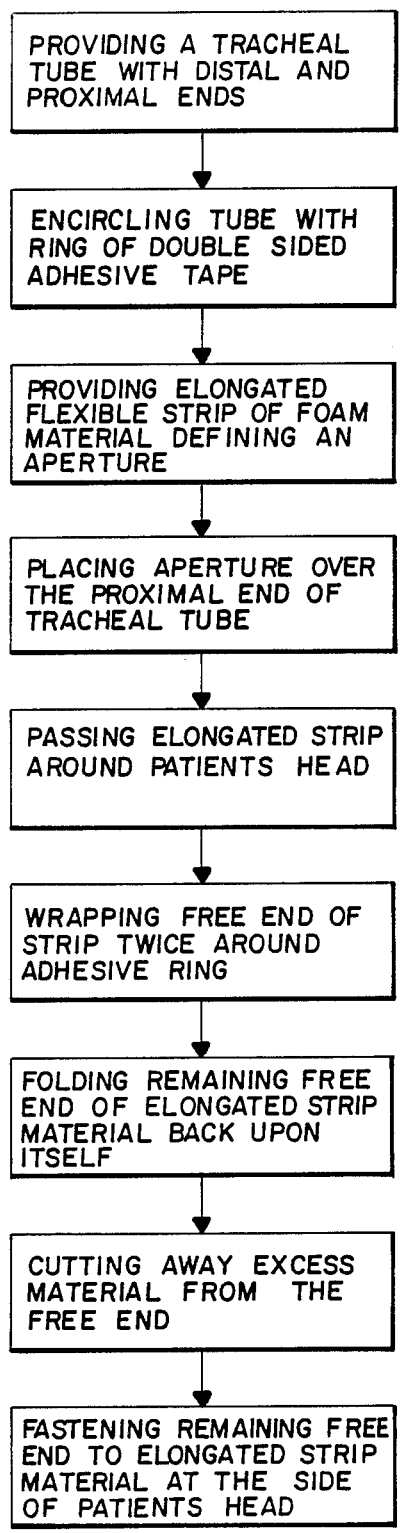

An improved method for holding a trachael tube or the like in an intubated position in a patient is illustrated in FIGS. 3. As illustrated, the method includes the step of providing a trachael tube or the like having proximal and distal ends. The distal end is adapted to be intubated into a patient with the proximal end extending outside of the patients mouth.

A ring of adhesive is formed around the circumference of the tube near the proximal end thereof i.e. in the area that extends outside of the patient's mouth and slightly removed from the patients lips. THis adhesive ring may be formed before or after intubation. However, if the ring is placed on the tube before intubation, it should be covered with a peelable nonadhesive film which can be readily removed after intubation. If the adhesive ring is placed around the tube after intubation, any mucus or other moisture is removed from the proximal end of the tube after intubation but before the tube is encircled with the band of double sided adhesive that is independent of an elongated strip.

The elongated flexible strip of foam material having a soft skin engaging material molded on one side thereof is also provided. This strip has a width which is about the same width as the adhesive ring and defines an aperture at one end thereof. This aperture is placed over the extending portion of the trachael tube with the porous side facing the patient. And then, that portion of the elongated strip which includes the aperture is pushed forwardly along the trachael tube into light engagement with the patient's lips with the porous side of the holder against the patients face.

In the preferred method, the ring of adhesive is applied to the trachael tube after intubation and after the aperture is placed over the end of the trachael tube as described. And then, the ring of adhesive is formed around the trachael tube in an area that is just above the elongated strip. This ring of adhesive is easily formed from a strip of double sided adhesive tape having a width which is about the same as the width of the elongated strip.

And then the elongated strip is pulled taught against the trachael tube and passed around the back of head of the patient using care to avoid any twisting of the elongated strip.

The end of the elongated strip after being passed around the patient's head is pulled taught and wrapped around the adhesive ring and the trachael tube in a slightly overlapping manner. It has been found that wrapping the elongated strip around the trachael tube one and one half times provides a secure hold on the tube i.e. fixes the tube in its preferred position.

The end of the elongated strip is then pulled back in the direction from which it had come and any excess length removed. For example, a short length of the remaining elongated strip may be cut away so that the remaining portions extend to an intermediate position along side of the patients head.

The free end is then fastened to the fabric mesh side of the elongated strip in a manner that helps secure the trachael tube in its proper position with respect to the patient.

The invention also contemplates a novel combination of a trachael tube or the like and an improved holder as defined above.

Although a preferred embodiment of the medical tube holder according to the present invention has been described, it should be recognized that various modifications may be made without departing from the scope of the claims. For example, the medical tube holder has been described in connection with a trachael tube, however, it may be used in combination with any tube which is inserted into a human body and temporarily fixed therein.

What is claimed is:

1. A method for holding a trachael tube or the like in an intubated position in a patient comprising the steps of:

(a) providing a trachael tube or the like having proximal and distal ends and intubating the distal end into the patient's air passage with the proximal end extending outside of the patient's body;
    (b) providing an elongated flexible strip of resilient fabric material having a foam skin engaging material molded on one side thereof and an aperture at one end thereof, and having a sufficient length to extend along the side of the patient's head after being wrapped around the patient's head or neck and wrapped one and one-half times around the trachael tube;
    (c) encircling the tube near its proximal end with a piece of double sided adhesive tape to thereby form an adhesive ring having about the same width as the width of the flexible strip of resilient fabric material and which is covered with a releasable non-adhesive film;
    (d) placing the aperture over the portion of the tube extending outside of the patient's body;
    (e) passing the flexible strip around the patient's head or neck with the skin engaging material against the patient's head or neck;
    (f) removing the releasable non-adhesive film;
    (g) wrapping the end of the flexible strip opposite the aperture around the tube and the adhesive ring at least one and one-half times in a partially overlapping manner to thereby hold the trachael tube in place;
    (h) cutting the free end of the elongated flexible strip so that the end thereof extends along the side of the patient's head or neck after being wrapped around the tube to an intermediate position on the side of the patient's head or neck; and
    (i) fastening the free end of the strip to the portion thereof at the intermediate positions along the side of the patient's head or neck.

2. A method for holding a trachael tube or the like in an intubated position in a patient according to claim 1 wherein any mucus or other moisture is removed from the proximal end of the tube after intubation but before step (c), and wherein the tube is encircled with a band of double sided adhesive that is independent of the elongated flexible strip.

3. A method for holding a trachael tube or the like in an intubated position in a patient according to claim 1 wherein the aperture of the elongated flexible strip of resilient foam skin engaging material is placed over the tube and the strip of resilient foam skin engaging material is forced downwardly into contact with the patient's lips and wherein the cutting in step (h) is done after the flexible strip is wrapped around the patient's head or neck and wrapped around the tube one and one half times; and pulling the free end back along the side of the patient's head without twisting.

* * * * *